(12) United States Patent
Larsen (10) Patent No.: US 9,826,969 B2
(45) Date of Patent: Nov. 28, 2017

(54) ADJUSTABLE SUTURE KNOT

(71) Applicant: DePuy Synthes Products, Inc., Raynham, MA (US)

(72) Inventor: Scott P. Larsen, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 323 days.

(21) Appl. No.: 14/789,559

(22) Filed: Jul. 1, 2015

(65) Prior Publication Data

US 2016/0000421 A1 Jan. 7, 2016

Related U.S. Application Data (60) Provisional application No. 62/020,765, filed on Jul. 3, 2014.

(51) Int. Cl.
*A61B 17/04* (2006.01)
*A61B 17/00* (2006.01)

(52) U.S. Cl.
CPC ......... *A61B 17/04* (2013.01); *A61B 17/0401* (2013.01); *A61B 2017/00526* (2013.01); *A61B 2017/0446* (2013.01); *A61B 2017/0474* (2013.01); *A61B 2017/0475* (2013.01); *A61B 2017/0477* (2013.01); *A61B 2017/0496* (2013.01)

(58) Field of Classification Search
CPC .... A61B 2017/0477; A61B 2017/0475; A61B 2017/0496; A61B 2017/0474; B65H 69/04; D04G 5/00; D04G 1/08
USPC .......................... 606/139, 144, 228; 289/1.2
See application file for complete search history.

(56) References Cited

U.S. PATENT DOCUMENTS

| | | | |
|---|---|---|---|
| 5,573,286 A | 11/1996 | Rogozinski | |
| 5,759,189 A | 6/1998 | Ferragamo et al. | |
| 2005/0043744 A1 | 2/2005 | Tu | |
| 2007/0083236 A1 | 4/2007 | Sikora et al. | |
| 2009/0076546 A1* | 3/2009 | Ashley ............... | A61B 17/0487 606/232 |

FOREIGN PATENT DOCUMENTS

WO 2004/069291 8/2004

OTHER PUBLICATIONS

International Search Report and Written Opinion (PCT/US2015/038756); dated Oct. 5, 2015.

* cited by examiner

*Primary Examiner* — Katherine M Shi
(74) *Attorney, Agent, or Firm* — Dunlap Codding, P.C.

(57) ABSTRACT

Knots and methods of forming knots made of flexible material for use in a surgical environment are described. The knots include one or more ways to unlock at least a portion of the knot.

12 Claims, 13 Drawing Sheets

ADJUSTABLE SUTURE KNOT

CROSS REFERENCE TO RELATED APPLICATION

This application claims priority to U.S. Provisional Application Ser. No. 62/020,765, filed Jul. 3, 2014, the entire content of which is hereby expressly incorporated herein by reference.

BACKGROUND

Sutures, and knots to secure and lock sutures, have been utilized for thousands of years. Most knots are locking knots, and are generally designed to be "one-way" meaning that they may not be able to be unlocked without untying them. Such static knots (e.g., surgeon's knot) are the predominate knots used in open surgical settings. In some applications, however, the ability to unlock the surgical knot may aid the surgeon.

Within the arthroscopic field, a few locking knots are employed that are capable of being unlocked. For example, the Tennessee Slider knot, the SMC knot, and the Roeder knot. Such sliding knots, however, are usually delivered down a cannula. Additionally, the sliding knots may also incorporate a tension device (e.g., endo-button).

DETAILED DESCRIPTION OF EXEMPLARY EMBODIMENTS

Before explaining at least one embodiment of the presently disclosed and claimed inventive concepts in detail, it is to be understood that the presently disclosed and claimed inventive concepts are not limited in their application to the details of construction, experiments, exemplary data, and/or the arrangement of the components set forth in the following description or illustrated in the drawings. The presently disclosed and claimed inventive concepts are capable of other embodiments or of being practiced or carried out in various ways. Also, it is to be understood that the phraseology and terminology employed herein is for purpose of description and should not be regarded as limiting.

In the following detailed description of embodiments of the inventive concepts, numerous specific details are set forth in order to provide a more thorough understanding of the inventive concepts. However, it will be apparent to one of ordinary skill in the art that the inventive concepts within the disclosure may be practiced without these specific details. In other instances, certain well-known features may not be described in detail to avoid unnecessarily complicating the instant disclosure.

As used herein, the terms "comprises," "comprising," "includes," "including," "has," "having," or any other variation thereof, are intended to cover a non-exclusive inclusion. For example, a process, method, article, or apparatus that comprises a list of elements is not necessarily limited to only those elements but may include other elements not expressly listed or inherently present therein.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

The term "and combinations thereof" as used herein refers to all permutations or combinations of the listed items preceding the term. For example, "A, B, C, and combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAAB-CCCC, CBBAAA, CABABB, and so forth. A person of ordinary skill in the art will understand that typically there is no limit on the number of items or terms in any combination, unless otherwise apparent from the context.

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

The use of the terms "at least one" and "one or more" will be understood to include one as well as any quantity more than one, including but not limited to each of, 2, 3, 4, 5, 10, 15, 20, 30, 40, 50, 100, and all integers and fractions, if applicable, therebetween. The terms "at least one" and "one or more" may extend up to 100 or 1000 or more, depending on the term to which it is attached; in addition, the quantities of 100/1000 are not to be considered limiting, as higher limits may also produce satisfactory results.

Further, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein qualifiers such as "about," "approximately," and "substantially" are intended to signify that the item being qualified is not limited to the exact value specified, but includes some slight variations or deviations therefrom, caused by measuring error, manufacturing tolerances, stress exerted on various parts, wear and tear, and combinations thereof, for example.

As used herein, the term "patient" is meant to include all organisms, whether alive or dead, including any species having soft tissues and bones. For example, a method according to the inventive concepts disclosed herein may be used to repair a soft tissue detachment injury in a living human, horse, cow, sheep, cat, dog, and the like. In another example, a method according to the inventive concepts disclosed herein may be used in a non-living organism to train medical personnel in surgical techniques. As yet another example, a method according to the instant disclosure may be used to implant medical devices such as replacement joints, pacemakers, and the like, into an organism by anchoring such devices to a bone. As yet another example, a method according to the inventive concepts disclosed herein may be used to repair the syndesmosis, or to repair various knee, elbow, hip, wrist, ankle, or other soft tissue detachment and tendon, joint, and/or ligament injuries.

Figure 1:
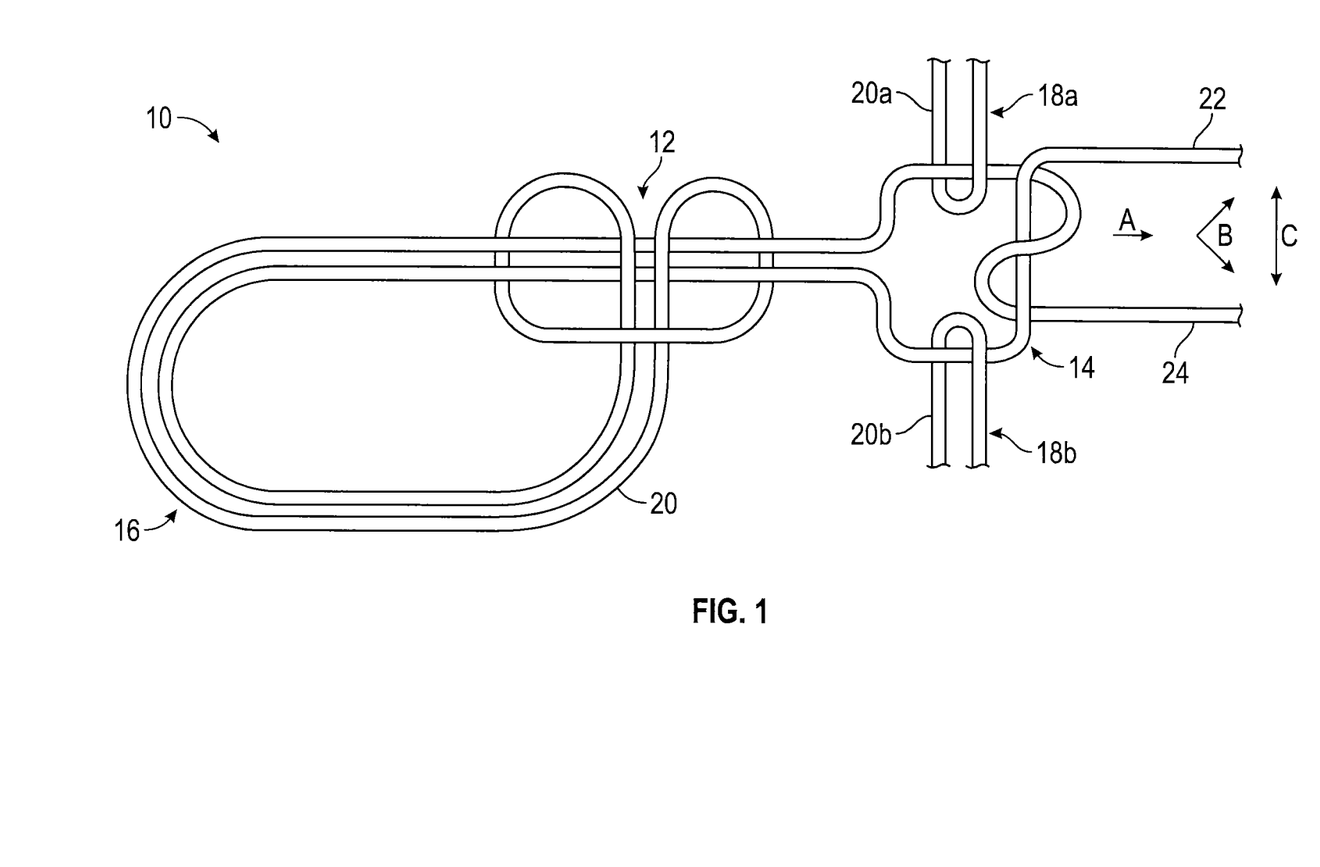
FIG. 1 is a schematic view showing an exemplary knot constructed in accordance with the present disclosure.

Referring now to the drawings, and in to particular FIG. 1, shown therein is a knot 10 formed in accordance with the present disclosure. The knot 10 generally comprises a slip knot 12, a half hitch knot 14, and an active loop 16. The knot 10 may also include one or more unlocking and/or loosening elements. For example, the knot 10 in FIG. 1 includes adjusting loops 18 for aiding in unlocking and/or loosening the knot 10. Adjusting loops 18 may be positioned between the slip know 12 and the half hitch knot 14.

Figure 2:
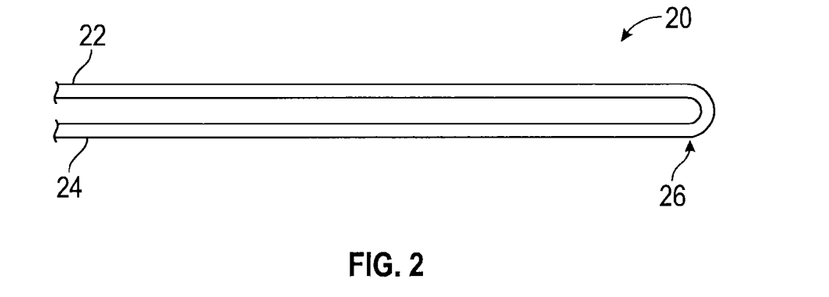
FIGS. 2-5 are schematic views showing formation of the knot illustrated in FIG. 1.

Referring to FIGS. 1 and 2, the knot 10 may be formed of one or more strands 20 of flexible material. Flexible material may include, but is not limited to, suture, thread, wire, cable, cord, rope and/or band. Each strand 20 may have two or more free ends defining a distal end of the knot 10. For example, in FIG. 2, the strand 20 includes free ends 22 and 24. Strand 20 may form the slip knot 12, the half hitch knot 14, and the active loop 16 of the knot 10 as shown in FIG. 1.

Figure 3:
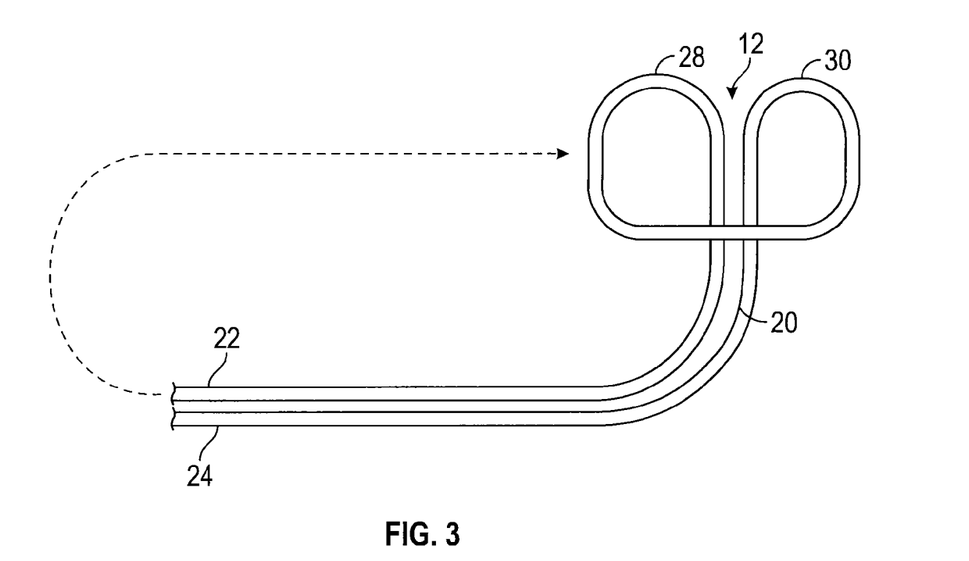
Figure 4:
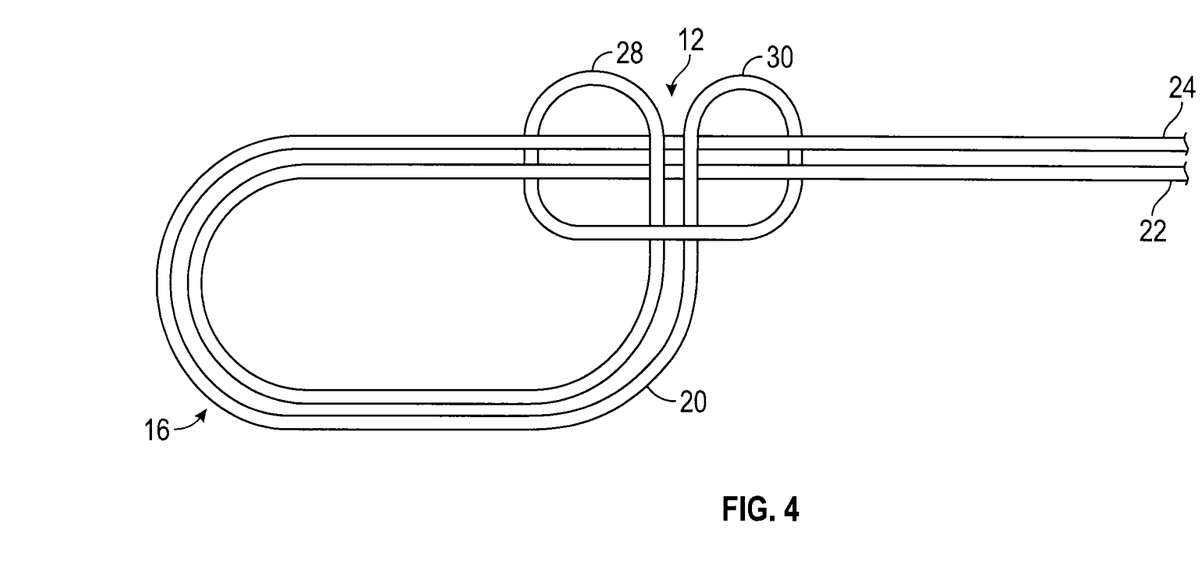

FIGS. 2-4 illustrate the general formation of the slip knot 12 and the active loop 16 of the knot 10 of FIG. 1. Referring to FIGS. 2 and 3, the strand 20 may be positioned to form a U-shaped curve 26 such that the free ends 22 and 24 are aligned adjacent to one another. The U-shaped curve 26 may be folded against the strand 20 forming two symmetrical loops 28 and 30.

Referring to FIGS. 3 and 4, the free ends 22 and 24 may be threaded through each symmetrical loop 28 and 30. Threading the free ends 22 and 24 through each symmetrical loop 28 and 30 forms the slip knot 12 and the active loop 16.

Figure 5:
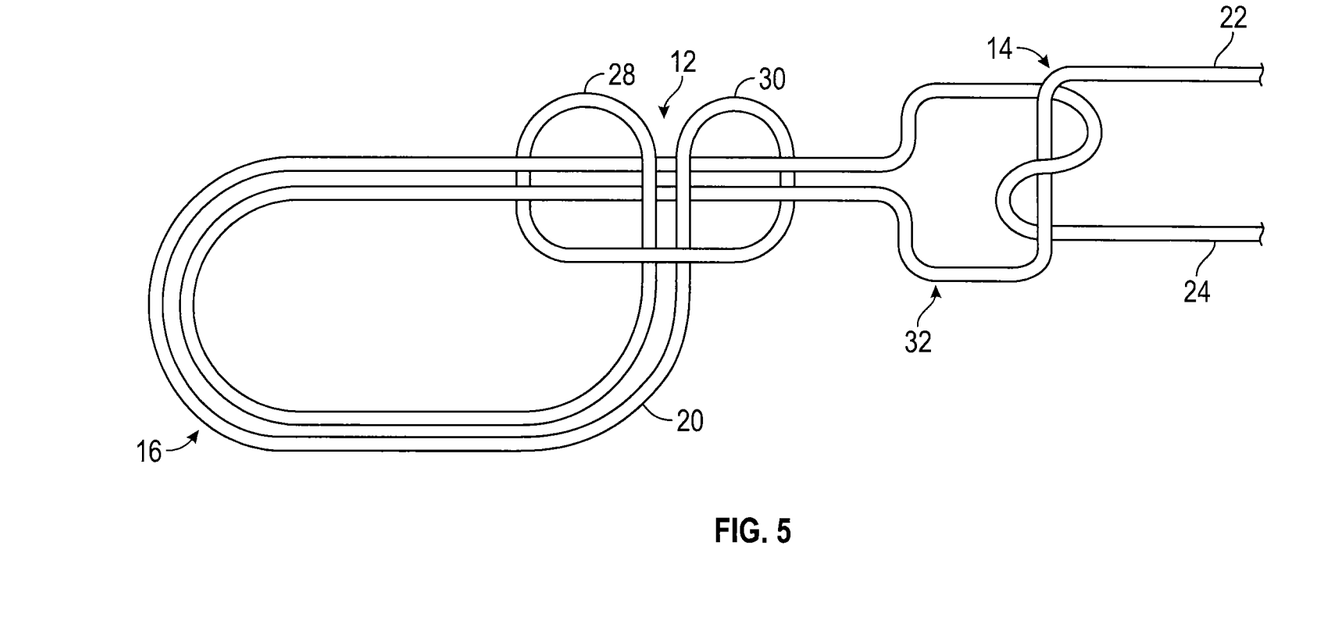

Referring to FIG. 5, the free ends 22 and 24 may be used to form the half hitch knot 14. Although the half hitch knot 14 is used in the knot 10 of FIGS. 1 and 5, it should be known that any overhand knot may be used. In forming the half hitch knot 14, a transition loop 32 may be formed between the slip knot 12 and the half hitch knot 14.

Figure 6:
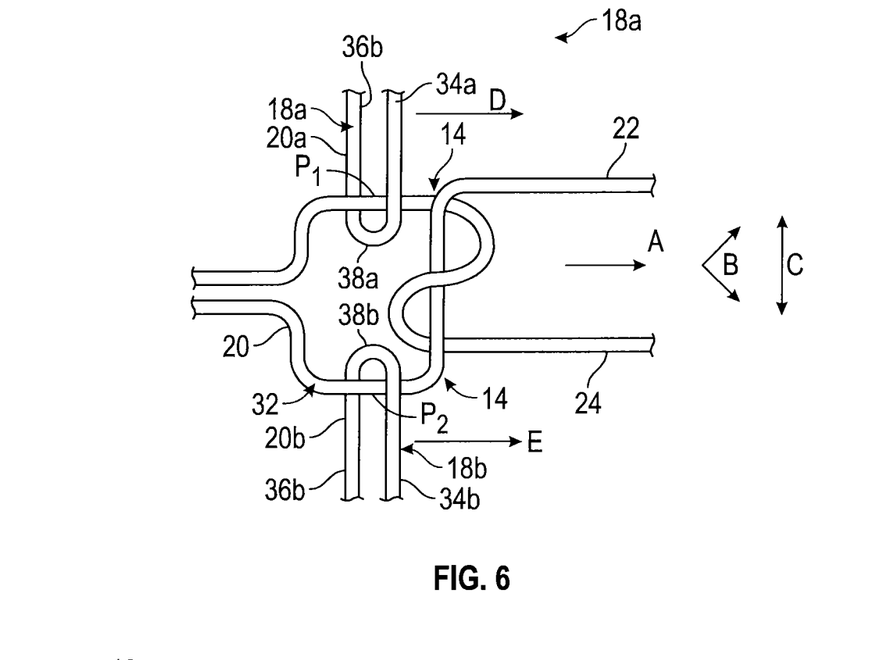
FIG. 6 is a schematic view showing exemplary adjusting loops for use in the knot illustrated in FIG. 1.

Referring to FIG. 6, the slip knot 12, half hitch knot 14, and the active loop 16 may be tightened by pulling on free ends 22 and 24 along different vectors (i.e., Vector A, Vector B, and Vector C). For example, by pulling on free ends 22 and 24 in the direction of Vector A, the active loop 16 may be tightened (i.e., reduced in size). In another example, by pulling on free ends 22 and 24 in the direction of Vector B or Vector C, the active loop 16 may tighten and the half hitch knot 14 may tighten locking the slip knot 12.

While the knot 10 may be progressively tightened and locked, the knot 10 may also be unlocked and/or loosened as described in further detail herein.

The knot 10 may include one or more adjusting loops formed of separate strands. For example, FIG. 6 illustrates two adjusting loops 18a and 18b formed of separate strands 20a and 20b, respectively. Strands 20a and 20b may be formed of flexible material. Flexible material may include, but is not limited to, suture, thread, wire, cable, cord, rope and/or band. In some embodiments, the strands 20, 20a, and/or 20b may be formed of similar material. In some embodiments, the strands 20, 20a and/or 20b may be formed of different materials.

Although the knot 10 illustrated in FIGS. 1 and 6 includes two adjusting loops 18a and 18b, it should be known that any number of adjusting loops may be used, including a single adjusting loop. For simplicity in description, two adjusting loops 18a and 18b will be described herein.

The adjusting loops 18a and 18b may be positioned between the slip knot 12 and the half hitch knot 14 within the transition loop 32. For example, as illustrated in FIG. 6, in some embodiments, adjusting loops 18a and 18b may be positioned at opposing points $P_1$ and $P_2$ on the transition loop 32. In some embodiments, multiple adjusting loops may be positioned on each opposing point $P_1$ and/or $P_2$. In some embodiments, multiple adjusting loops may be positioned along the strand 20 spanning the length between the slip knot 12 and the half hitch knot 14. For example, multiple adjusting loops may be positioned along the strand 20 at multiple points (e.g., $P_1$, $P_2$ . . . $P_x$). In some embodiments, multiple points may be positioned such that each point P has an opposing point along the transition loop 32 having adjusting loops thereon. In some embodiments, multiple points may be random along the transition loop 32.

Each strand 20a and 20b of each adjusting loop 18a and 18b, respectively, may include free ends connected by a curve in a U-shaped pattern. For example, in FIG. 6, the strand 20a of adjusting loop 18a includes free ends 34a and 36a connected by a curve 38a. Similarly, the strand 20b of adjusting loop 18b includes free ends 34b and 36b connected by a curve 38b.

Each curve 38a and 38b of each adjusting loop 18a and 18b may overlap the strand 20 at the transition loop 32. For example, the curve 38a may overlap the strand 20 such that the curve 38a bends around the strand 20 at the transition loop 32 and the free ends 34a and 36a are positioned adjacent to each other. Similarly, the curve 38b may overlap the strand 20 such that the curve 38b bends around the strand 20 at the transition loop 32 and the free ends 34b and 36b are positioned adjacent to each other.

The adjusting loops 18a and 18b may be used to aid in unlocking and/or loosening the knot 10. More particularly, the adjusting loops 18a and 18b may be used to unlock and/or loosen the half hitch knot 14 of the knot 10.

As described herein, by pulling on free ends 22 and 24 in the direction of Vector B or Vector C, the active loop 16 may tighten and the half hitch knot 14 may also tighten locking the slip knot 12. To loosen and/or unlock the half hitch knot 14, each adjusting loop 18a and 18b may be pulled towards the half hitch knot 14 such that each adjusting loop exerts force on the half hitch knot 14 loosening and/or unlocking the half hitch knot 14. For example, as illustrated in FIG. 6, the free ends 34a and 36a, and the free ends 34b and 36b may be pulled in the direction of Vectors D and/or E respectively to loosen and/or unlock the half hitch knot 14.

Figure 7:
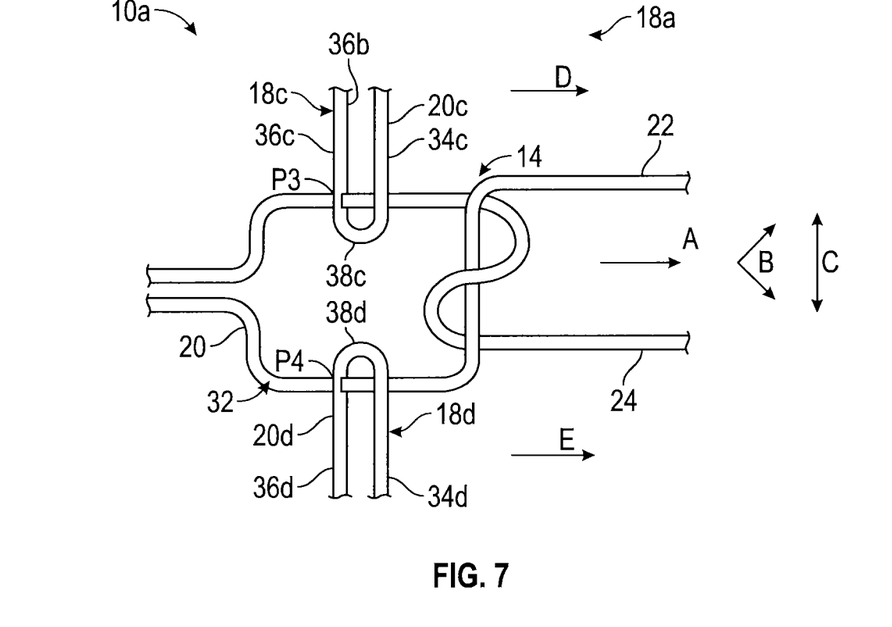
FIG. 7 is a schematic view showing exemplary adjusting loops received within the knot illustrated in FIG. 1.

FIG. 7 illustrates another exemplary embodiment of a knot 10a having one or more adjusting loops through which the strand 20 is stitched or passed. For example, the knot 10a illustrated in FIG. 7 includes the strand 20 passed through the two adjusting loops 18c and 18d. In some embodiments, the knot 10a may include the strand 20 passed through a single adjusting loop 18c. For simplicity in description, the strand 20 being passed through two adjusting loops 18c and 18d will be described herein.

Each strand 20c and 20d of each adjusting loop 18c and 18d may include free ends connected by a curve in a U-shaped pattern. For example, in FIG. 7, the strand 20c of the adjusting loop 18c includes free ends 34c and 36c connected by a curve 38c. Similarly, the strand 20d of the adjusting loop 18d includes free ends 34b and 36b connected by a curve 38b.

The strands 20c and 20d of the adjusting loops 18c and 18d, respectively, may receive the strand 20 at one or more points along the strand 20 between the slip knot 12 and the half hitch knot 14 within the transition loop 32. For example, as illustrated in FIG. 7, in some embodiments, adjusting loops 18c and 18d may receive the strand 20 at points $P_3$ and $P_4$ on the transition loop 32. In this example, the strand 20 may be known as the shuttle strand with the strands 20c and 20d known as ground strands. In other embodiments, the strand 20 may be passed through multiple adjusting loops at or adjacent to each opposing point $P_3$ and/or $P_4$ or along the strand 20 spanning the length between the slip knot 12 and the half hitch knot 14. For example, multiple adjusting loops receive the strand 20 at multiple points (e.g., $F_1, P_2 \ldots P_x$). In some embodiments, multiple ground strands may receive the shuttle strand 20 such that each point P has an opposing point along the transition loop 32 having a round strand receiving the shuttle strand 20.

The adjusting loops 18c and 18d may be used to aid in unlocking and/or loosening the knot 10a. More particularly, the adjusting loops 18c and 18d may be used to unlock and/or loosen the half hitch knot 14 of the knot 10a.

As described herein, by pulling on free ends 22 and 24 in the direction of Vector B or Vector C, the active loop 16 may tighten and the half hitch knot 14 may tighten locking the slip knot 12. Each adjusting loop 18c and 18d may be pulled towards the half hitch knot 14 such that each adjusting loop exerts force on the half hitch knot 14 loosening and/or unlocking the half hitch knot 14. For example, as illustrated in FIG. 7, the free ends 34c and 36c, and the free ends 34d and 36d may be pulled in the direction of Vectors D and/or E, respectively, to loosen and/or unlock the half hitch knot 14.

Figure 8:
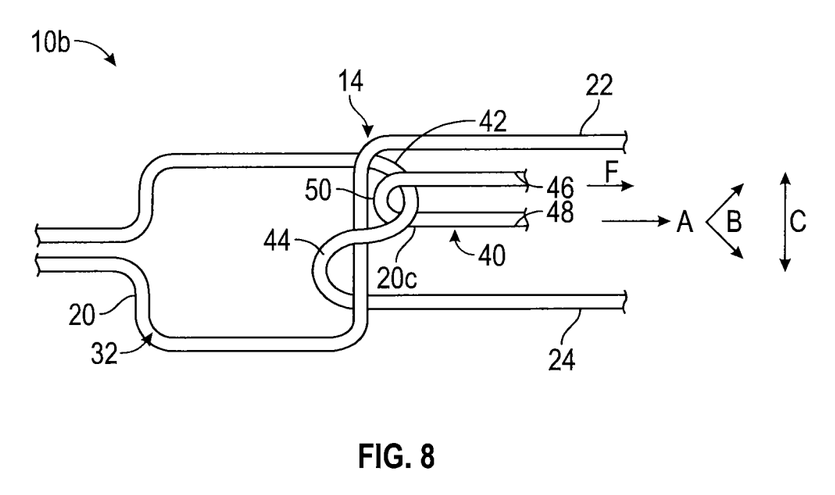
FIG. 8 is a schematic view showing an exemplary adjusting loop for use in the knot illustrated in FIG. 1.

FIG. 8 illustrates another exemplary embodiment of a knot 10b having one or more adjusting loops 40 positioned within the half hitch knot 14. Generally, the half hitch knot 14 may include a proximal loop 42 and a distal loop 44. The one or more adjusting loops 40 may be positioned on the proximal loop 42 of the half hitch knot 14, and the adjusting loop 40 may be pulled in a direction proximal to the half hitch knot 14 to loosen and/or unlock the half hitch knot 14.

Referring to FIG. 8, the adjusting loop 40 may be formed of a strand 20c separate from the strand 20. The strand 20c may be formed of flexible material. Flexible material may include, but is not limited to, suture, thread, wire, cable, cord, rope and/or band. In some embodiments, the strand 20c may be formed of different material than the strand 20.

The strand 20c may include free ends 46 and 48 with a U-shaped curve 50 connecting the free ends. The curve 50 may overlap the strand 20 at the proximal loop 42 of the half hitch knot 14. For example, the curve 50 may overlap the strand 20 such that the curve 50 bends around the strand 20 about the proximal loop 42 and the free ends 46 and 48 are positioned adjacent to each other.

As described herein, by pulling on free ends 22 and 24 in the direction of Vector B or Vector C, the active loop 16 may tighten and the half hitch knot 14 may tighten locking the slip knot 12. To loosen and/or unlock the half hitch knot 14, the adjusting loop 40 may be pulled in a direction distal to the half hitch knot 14 such that the adjusting loop exerts force on the half hitch knot 14 loosening and/or unlocking the half hitch knot 14. For example, as illustrated in FIG. 8, the free ends 46 and 48 may be pulled in the direction of Vector F to loosen and/or unlock the half hitch knot 14.

Figure 9:
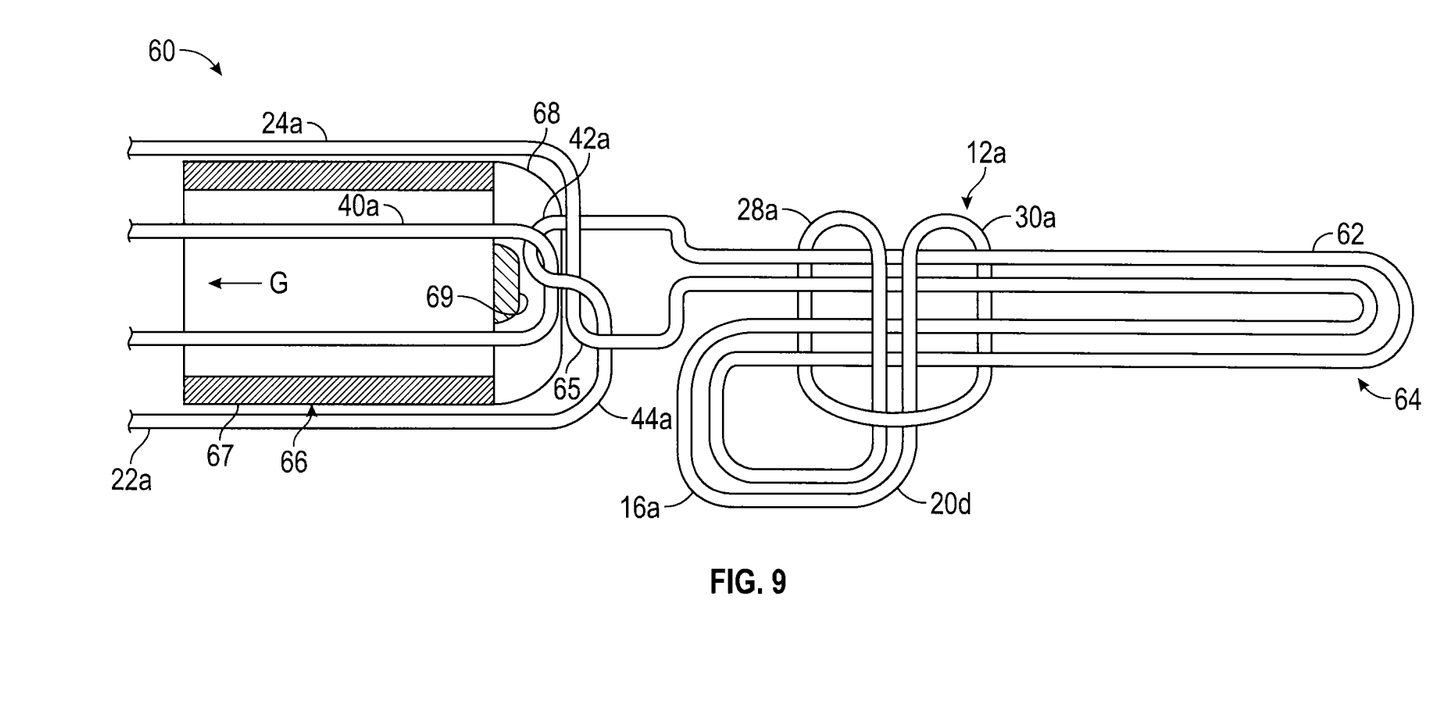
FIG. 9 is a schematic view showing another embodiment of a knot constructed in accordance with the present disclosure.

FIG. 9 illustrates an embodiment of a knot 60 wherein a strand 62 forms a slip knot 12a and an active loop 16a similar to the formation of the slip knot 12 and the active loop 16 shown in FIG. 4. After formation of the slip knot 12a and the active loop 16a, however, the free ends 22a and 24a may be threaded again through the symmetrical loops 28a and 30a of the slip knot 12 as shown in FIG. 9. Re-threading of the free ends 22a and 24a through the symmetrical loops 28a and 30a of the slip knot 12 may form a second loop 64. In some embodiments, after formation of the second loop 64, the free ends 22a and 24a may also be made to form a half hitch knot 65 as described in further detail herein.

By pulling on free ends 22a and 24a in the direction of vector G, the active loop 16a and the second loop 64 may both tighten and/or reduce in size. In some embodiments, the second loop 64 may be loosened without expanding the active loop 16a. For example, tension may be placed on the strand 20d at the second loop 64 and pulled in a direction away from the slip knot 12 such that the second loop 64 is loosened.

In one example, the knot 60 may be implemented in an orthopedic surgical application wherein two or more anchors are positioned within bone. For example, a first anchor may be positioned within a tibia and a second anchor may be positioned within a fibula. To that end, the second loop 64 of the knot 60 may be attached to the first anchor within the tibia, and the active loop 16a of the knot 60 may be attached to the second anchor within the fibula. By pulling of the free ends 22a and 24b, both the second loop 64 and the active loop 16a may collapse (i.e., reduce in size). The second loop 64 attached to the first anchor within the tibia may be loosened without the active loop 16a expanding. This may provide for reduction facilitation.

In FIG. 9, the knot 10b is shown to have an adjusting loop 40a positioned within the half hitch knot 65. Generally, the half hitch knot 65 may include a proximal loop 42a and a distal loop 44a. The adjusting loop 40a may be positioned on the proximal loop 42a of the half hitch knot 65, and the adjusting loop 40a may be pulled in a direction proximal to the half hitch knot 65 to loosen and/or unlock the half hitch knot 65.

In one embodiment, the adjusting loop 40a may be connected to a knot pusher 66 (schematically illustrated in FIG. 9). In one embodiment, the knot pusher 66 may include a tubular body 67 and a pusher head 68 extending from a distal end of the tubular body 67. The pusher head 68 may be provided with one or more grooves 69 for receiving and supporting the curve of the adjusting loop 40a. The free ends of the adjusting loop 40a may pass through the tubular body 67 and be detachably connected to a proximal end of the tubular body 67 in a suitable manner so that the adjusting loop 40a may be removed from the half hitch knot 65 when desired. In one embodiment, the ends of the adjusting loop 40a can be captured underneath a head of a bolt member (not shown) that is on a handle of the knot pusher 66. When the bolt is loosened, the adjusting loop 40a is free to be removed from the half hitch knot 65. In another version, the ends of the adjusting loop 40a can be captured in a cleat (not shown) on the handle of the knot pusher 66. In yet another version, the ends of the adjusting loop 40a can be tied or glued to the handle of the knot pusher 66. To free the adjusting loop 40a from the half hitch knot 65, the adjusting loop 40a can be cut.

By pushing the knot pusher 66 and pulling on free ends 22a and 24a in the direction of vector G, the active loop 16a and the second loop 64 may both tighten and/or reduce in size and the half hitch knot 65 may tighten locking the slip knot 12a. To loosen and/or unlock the half hitch knot 65, the adjusting loop 40a may be pulled in a direction distal to the half hitch knot 14 by pulling on the knot pusher 66 such that the adjusting loop exerts force on the half hitch knot 65 loosening and/or unlocking the half hitch knot 65. The half hitch knot 65 may then be tightened again. Upon obtaining the final adjustment, the adjusting loop 40 may be removed from the proximal loop 42a.

FIGS. 10A-10E illustrate formation of a stitch lock knot 70. The stitch lock knot 70 may be capable of being repeatedly locked and unlocked in accordance with the present disclosure.

Figure 10A:
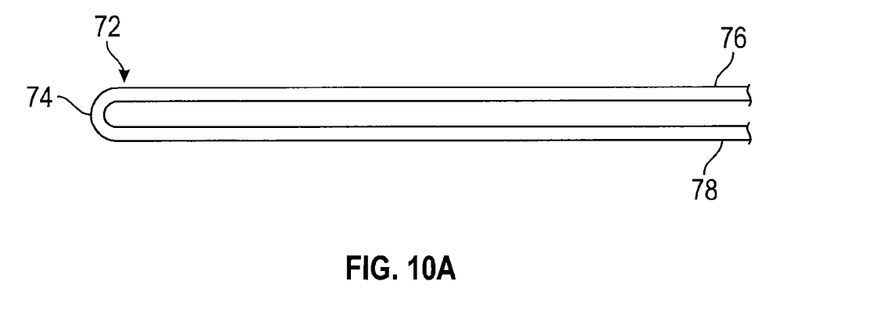
FIGS. 10A-10E illustrate schematic views showing formation of an exemplary knot for use in accordance with the present disclosure.

Referring to FIG. 10A, the stitch lock knot 70 may be formed from a strand 72. The strand 72 may be positioned to form a u-shaped curve 74 such that free ends 76 and 78 are aligned adjacent to one another. Herein, free end 76 may be used interchangeably with the term tension strand and free end 78 may be used interchangeably with the term lock strand.

Figure 10B:
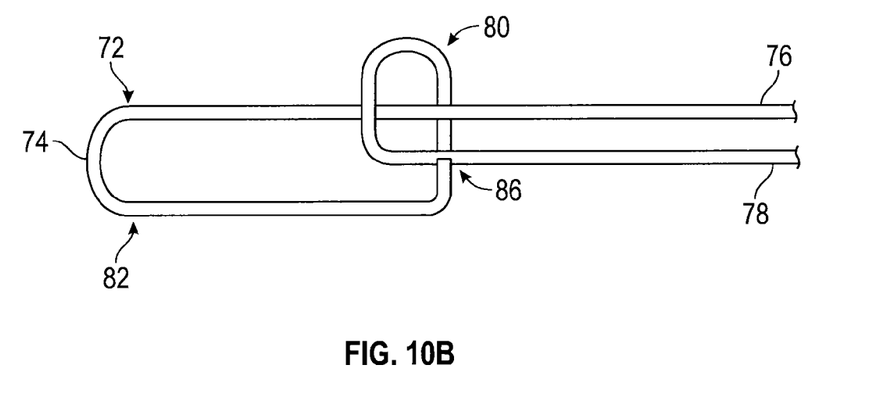

Referring to FIG. 10B, a stitch loop 80 and active loop 82 may be formed in the strand 72. The stitch loop 80 may be formed by piercing or passing the strand 76 through strand 78 at area 86. The strand 76 may then be passed through the loop 80, as illustrated in FIG. 10B.

Figure 10C:
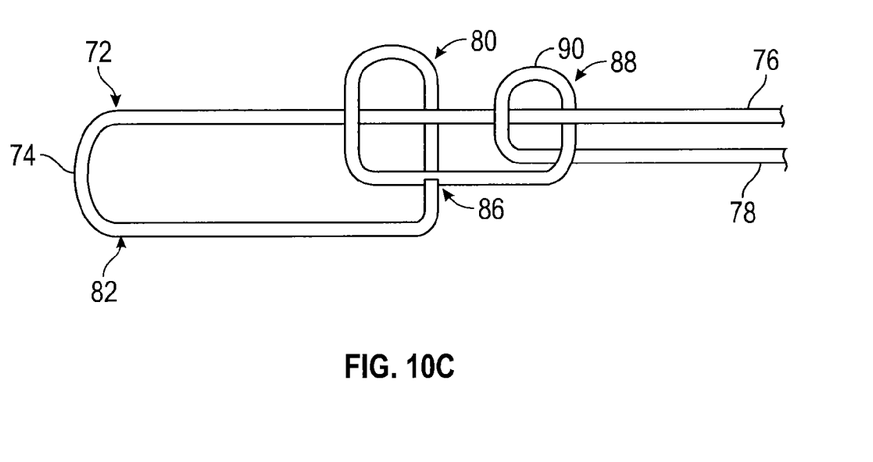

As illustrated in FIG. 10C, an overhand loop 88 may be formed in the strand 72. The overhand loop 88 may be formed by looping the lock strand 78 about the tension strand 76 forming a curve 90. The curve 90 may bend about the tension strand 76. Distal to the overhand loop 88, the lock strand 78 and the tension strand 76 may be positioned adjacent to one another.

Figure 10D:
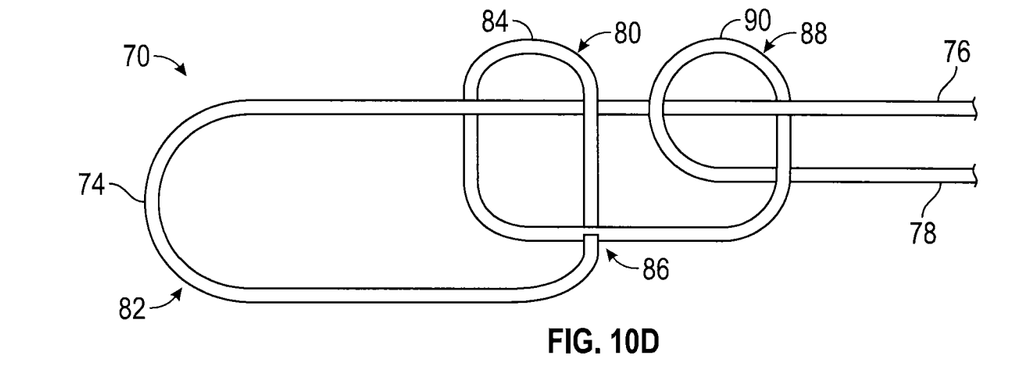
Figure 11A:
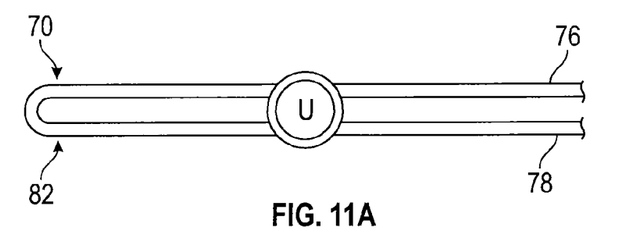
FIGS. 11A-11E illustrate schematic views of locking and unlocking capabilities of the knot illustrated in FIGS. 10A-10E.
Figure 11B:
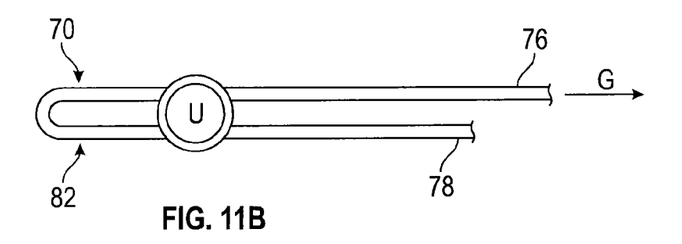

Referring to FIG. 10D, generally, the stitch lock knot 70 comprises the stitch loop 80 and the overhand loop 88. The tension strand 76 of the stitch lock knot 70 may be used to control size and/or tension of the active loop 82. For example, as illustrated in FIGS. 11A and 11B, if the stitch knot 80 is unlocked, the tension strand 76 may be capable of freely sliding through the stitch loop 80 and the overhand loop 88 allowing for the active loop 82 to increase or reduce in size. For example, with the stitch lock knot 70 unlocked, the tension strand 76 may be pulled in direction of vector G reducing the size of the active loop 82.

Figure 10E:
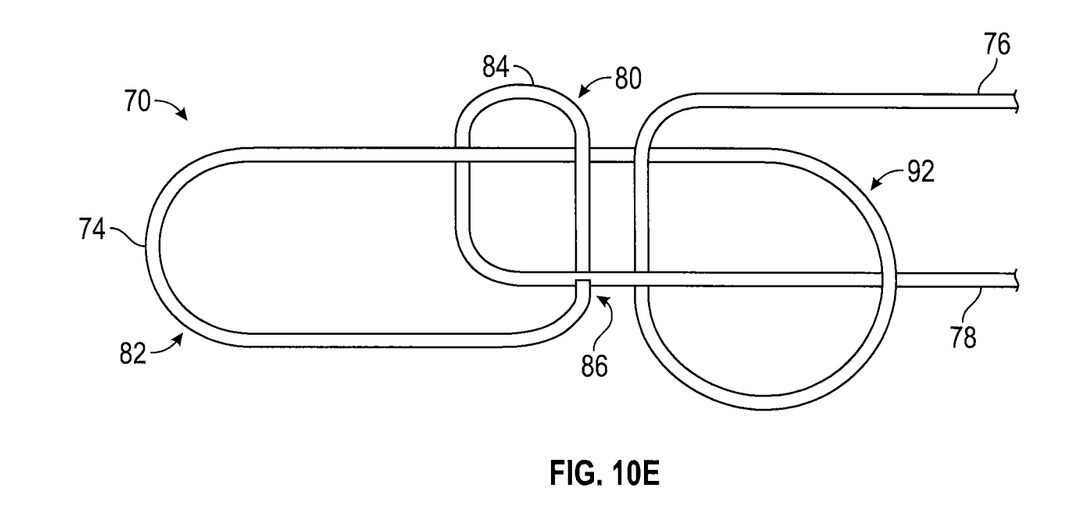
Figure 11C:
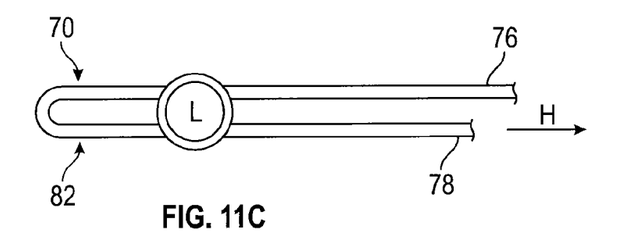

Referring to FIGS. 10E and 11C, to lock the stitch lock knot 70, tension may be applied to the lock strand 78. For example, tension may be applied to the lock strand 78 in direction of vector H. If tension is applied to the lock strand 78, for example, the overhand loop may become inverted as illustrated in FIG. 10E forming inverted loop 92. The inverted loop 92 positions the tension strand 76 within a torturous path and locks the stitch lock knot 70.

Figure 11D:
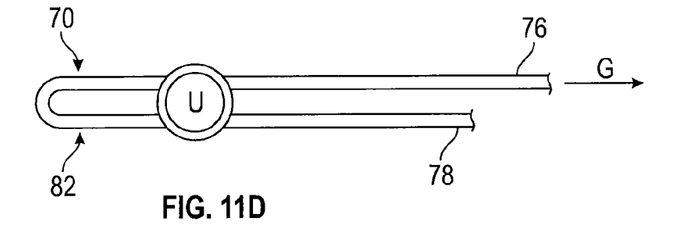
Figure 11E:
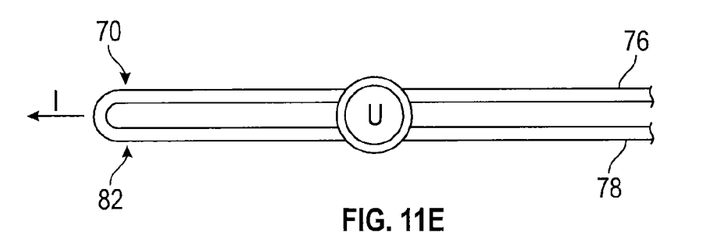

Referring to FIG. 11D, the stitch lock knot 70 may be unlocked by applying tension to the tension strand 76. For example, tension applied to the tension strand 76 in the direction of vector G may unlock the locked stitch lock knot 70 by inverting the overhand loop. FIG. 11E illustrates the stitch lock knot 70 within the unlocked state, wherein the active loop 82 may now be adjusted in size. In this example, tension may be applied on the active loop 82 in the direction of vector I to increase the size of the active loop 82.

Figure 12A:
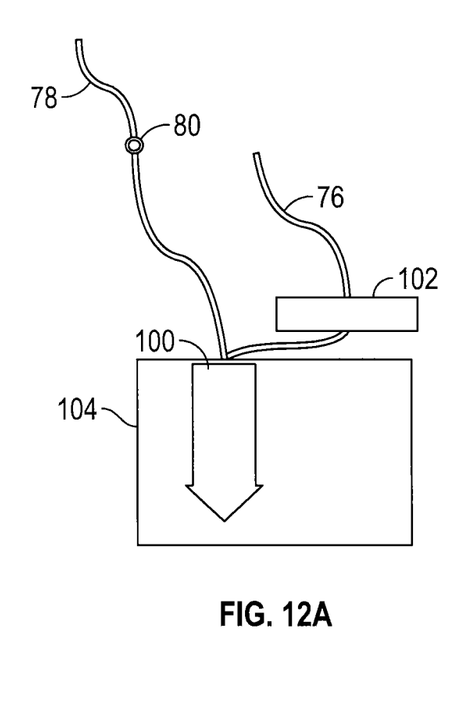
FIGS. 12A-12C illustrate schematic views of an exemplary use of the knot illustrated in FIGS. 10A-10E wherein the knot aids in connecting soft tissue to bone.
Figure 12B:
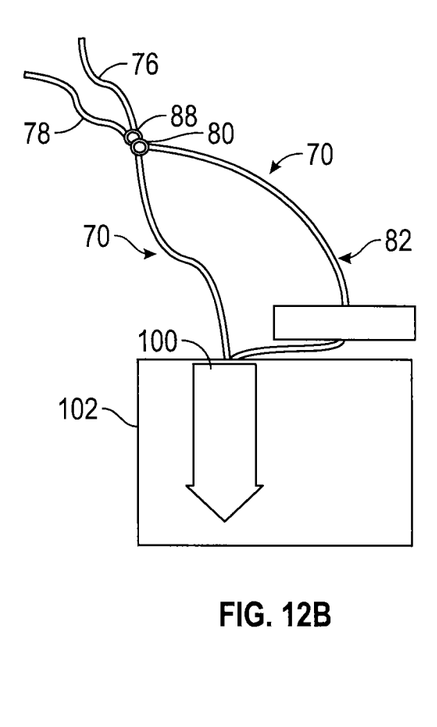
Figure 12C:
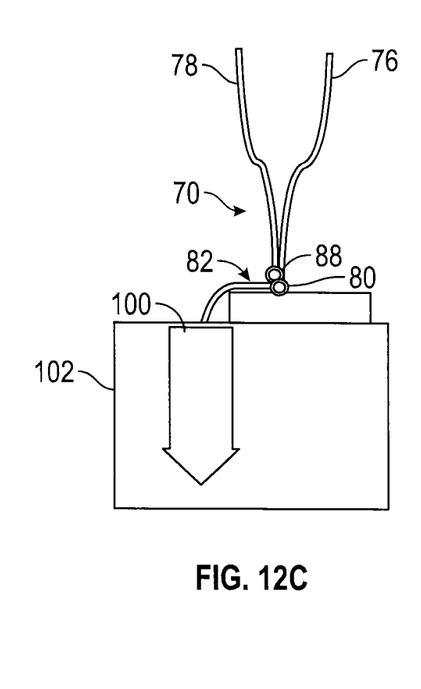

In some embodiments, the stitch lock knot 70 may be used to repair various knee, elbow, hip, wrist, ankle, or other soft tissue detachment and tendon, joint, and/or ligament injuries. For example, FIGS. 12A-12C illustrate an exemplary method for using the stitch lock knot 70 with a suture anchor 100 to attach soft tissue 102 to bone 104 or bone to bone. FIG. 12A illustrates the suture anchor 100 positioned within bone 104. The lock strand 78 may be attached to the suture anchor 100. For example, in some embodiments, the lock strand 78 may be threaded through a portion of the suture anchor 100. The lock strand 78 may include a pre-formed stitch loop 80. The tension strand 76 may be attached to the soft tissue 102. For example, the tension strand 76 may be threaded through the soft tissue 102.

Referring to FIG. 12B, the tension strand 76 may be threaded through the pre-formed stitch loop 80 on the lock strand 78 forming active loop 82. The hatch-hitch loop 88 may then be formed as described herein forming the stitch lock. The tension strand 76 may be pulled to reduce the size of the active loop 82 bringing the soft tissue 102 adjacent to the bone 104. The stitch lock knot 70 may be further tightened, locked, unlocked, and/or adjusted as described in further detail herein.

Figure 13A:
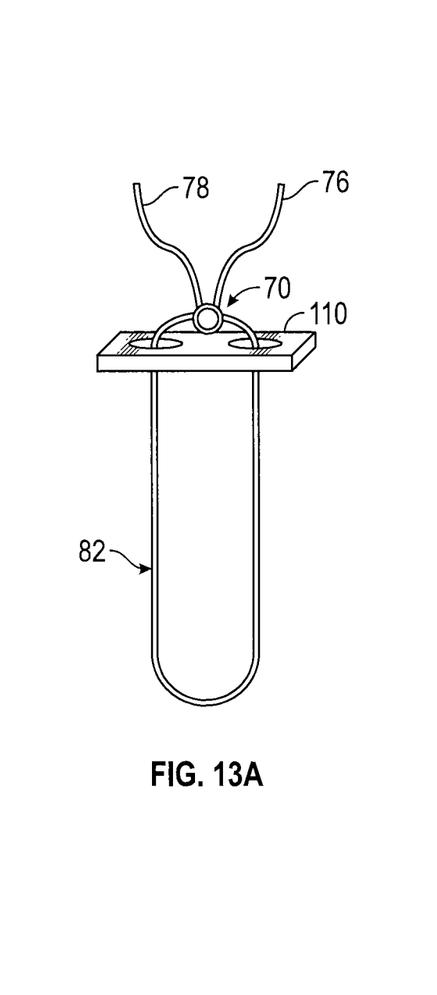
FIGS. 13A-13C illustrate schematic views of exemplary uses of the knots illustrated herein within a surgical environment.
Figure 13B:
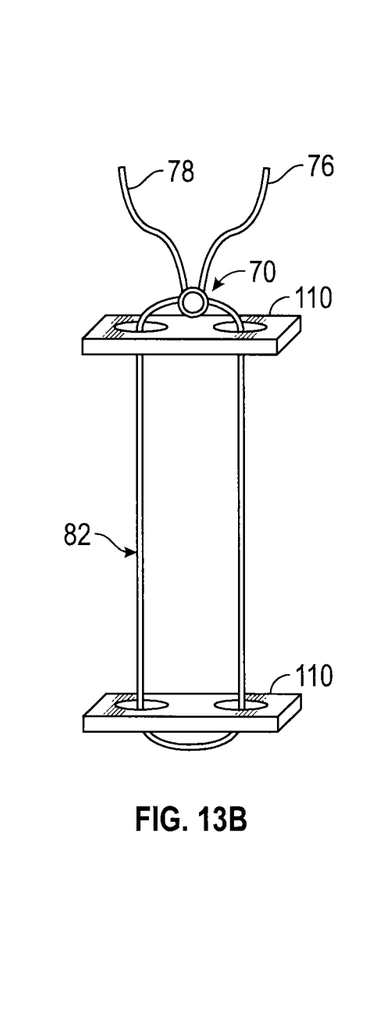
Figure 13C:
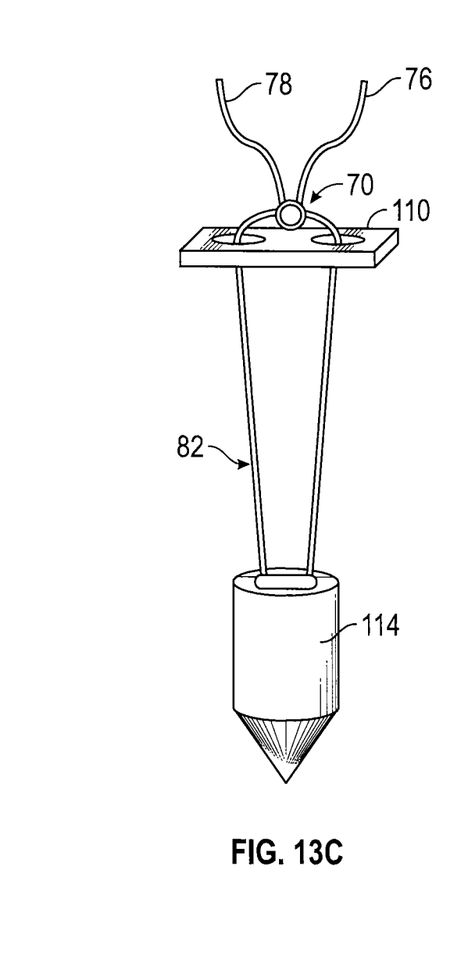

FIGS. 13A-13C illustrates additional exemplary orthopedic tension implants wherein a knot, such as the knots 10, 10a, 10b, 60, and 70 may be used to attach soft tissue to bone or bone to bone. For example, the stitch lock knot 70 may be used with buttons 110 as illustrated in FIGS. 13A and 13B wherein one or more buttons 110 may be positioned within the active loop 82. Alternatively, the stitch lock knot 70 may be used with a button-anchor construct with the button 110 and an anchor 114 positioned within the active loop 82. It should be noted that the stitch lock knot 70 is not intended to be limited to the examples provided and may be incorporated in any orthopedic tension implant or surgical application wherein locking and unlocking of the stitch lock knot 70 may aid in intra-operative reduction or procedure.

Figure 14:
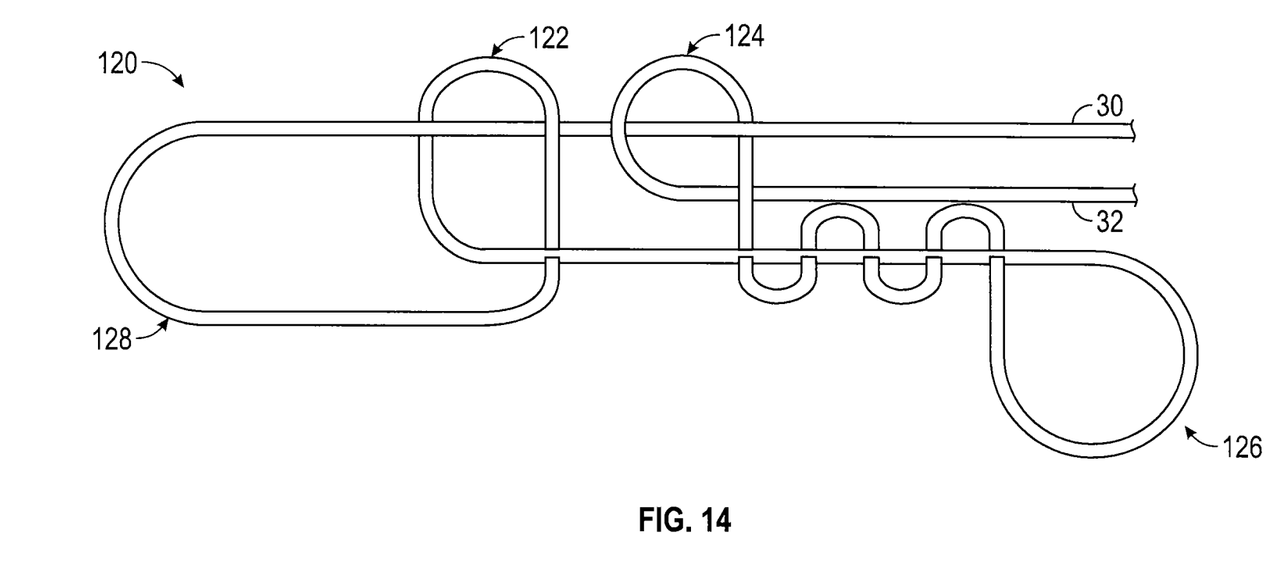
FIG. 14 illustrates a schematic view of another embodiment of a knot constructed in accordance with the present disclosure.

FIG. 14 illustrates an exemplary embodiment of a knot 120 having a stitch loop 122 and a overhand loop 124 similar to the stitch lock knot 70 illustrated in FIG. 10D. Knot 120 also includes a connector loop 126. The connector loop 126 may be formed to serve as a direct point of fixation, or capable of aiding other connectors and/or fixators for fixation. The connector loop 126 serves in addition to an active loop 128. In one example, the connector loop 126 may be formed using a static stitch loop such as shown in FIG. 14. In another example, the connector loop 126 may be formed by a bowline knot and/or loop.

Similar to the stitch lock knot 70 illustrated in FIG. 10D, the knot 120 in FIG. 14 may include a tension strand 130 and a lock strand 132. Unlocking and locking of the knot 120 may be performed by providing tension to the tension strand 130 and the lock strand 132 as described in further detail herein.

From the above description, it is clear that the inventive concepts disclosed and claimed herein are well adapted to carry out the objects and to attain the advantages mentioned herein, as well as those inherent in the invention. While exemplary embodiments of the inventive concepts have been described for purposes of this disclosure, it will be understood that numerous changes may be made which will readily suggest themselves to those skilled in the art and which are accomplished within the spirit of the inventive concepts disclosed and/or defined in the appended claims.

What is claimed is:

1. A knot, comprising:
a first strand of flexible material having two free ends defining a distal end, the first strand being in the form of a slip knot, a half hitch knot positioned distal the slip knot, and an active loop positioned proximal the slip knot; and
a second strand of flexible material associated with the first strand distal the slip knot in a way that tension applied to the second strand loosens the half hitch knot of the first strand.

2. The knot of claim 1, wherein the second strand forms a curve positioned about the first strand proximal the half hitch knot.

3. The knot of claim 2, further comprising a third strand of flexible material forming a curve positioned about the first strand of flexible material proximal the half hitch knot and in an opposing relationship to the second strand.

4. The knot of claim 1, wherein the first strand extends through the second strand proximal the half hitch knot.

5. The knot of claim 4, further comprising a third strand of flexible material, the first strand extending through the third strand proximal the half hitch knot and in an opposing relationship to the second strand.

6. The knot of claim 1, wherein the half hitch knot includes a distal loop and a proximal loop, and wherein the second strand of flexible material is positioned about the distal loop of the half hitch knot.

7. The knot of claim 6, further comprising a knot pusher, wherein the second strand is connected to the knot pusher.

8. The knot of claim 7, wherein the knot pusher has a tubular body and a pusher head extending from a distal end of the tubular body, the pusher head having one or more grooves formed therein, wherein the second strand is received in the groove of the pusher head and is detachably connected to the tubular body.

9. The knot of claim 1, wherein the first strand has another active loop formed distal of the slip knot.

10. The knot of claim 9, wherein the half hitch knot includes a distal loop and a proximal loop, and wherein the second strand of flexible material is positioned about the distal loop of the half hitch knot.

11. The knot of claim 10, further comprising a knot pusher, wherein the second strand is connected to the knot pusher.

12. The knot of claim 11, wherein the knot pusher has a tubular body and a pusher head extending from a distal end of the tubular body, the pusher head having one or more grooves formed therein, wherein the second strand is received in the groove of the pusher head and is detachably connected to the tubular body.

* * * * *